US009815001B2

(12) United States Patent
Massingill

(10) Patent No.: US 9,815,001 B2
(45) Date of Patent: Nov. 14, 2017

(54) USE OF A FIBER CONDUIT CONTACTOR FOR EXTRACTION

(71) Applicant: Chemtor, LP, San Marcos, TX (US)

(72) Inventor: John Lee Massingill, San Marcos, TX (US)

(73) Assignee: Chemtor, LP., San Marcos, TX (US)

( * ) Notice: Subject to any disclaimer, the term of this patent is extended or adjusted under 35 U.S.C. 154(b) by 0 days.

(21) Appl. No.: 15/277,533

(22) Filed: Sep. 27, 2016

(65) Prior Publication Data

US 2017/0014733 A1 Jan. 19, 2017

Related U.S. Application Data

(63) Continuation of application No. 14/030,760, filed on Sep. 18, 2013, now Pat. No. 9,468,866.
(Continued)

(51) Int. Cl.
*B01D 11/04* (2006.01)
*C02F 1/26* (2006.01)
(Continued)

(52) U.S. Cl.
CPC .......... *B01D 11/0449* (2013.01); *B01D 11/04* (2013.01); *C02F 1/26* (2013.01);
(Continued)

(58) Field of Classification Search
CPC ....... B01D 11/04; B01D 11/0449; C02F 1/26; C02F 2101/103; C02F 2101/20;
(Continued)

(56) References Cited

U.S. PATENT DOCUMENTS 2,164,663 A 7/1939 Ottofy
3,640,980 A 2/1972 Baba
(Continued)

FOREIGN PATENT DOCUMENTS

CN 1643116 7/2005
CN 1826403 8/2006
(Continued)

OTHER PUBLICATIONS

International Search Report & Written Opinion, PCT/US2013/060438, dated Feb. 7, 2014.
(Continued)

*Primary Examiner* — Dirk Bass
(74) *Attorney, Agent, or Firm* — Egan, Peterman, Enders & Huston LLP

(57) ABSTRACT

Processes are provided which utilize fiber conduit reactors/contactors to effect extraction from a fluid stream, particularly a fermentation broth, a waste stream of a fermentation process, a fluid comprising a dye, or a fluid comprising a pharmaceutical compound. In particular, methods are provided which include introducing a first stream comprising an extractant and a second stream which is substantially immiscible with the first stream into a conduit reactor proximate a plurality of fibers. The streams are introduced into the conduit reactor such that they are in contact with each other and the extractant of the first stream interacts with the second stream to extract a fermentation product, a fermentation byproduct, a dye or a pharmaceutical compound from the second stream into the first stream. The method further includes receiving the first and second streams in collection vessel/s and withdrawing separately the first and second streams from collection vessel/s.

20 Claims, 4 Drawing Sheets

Related U.S. Application Data

(60) Provisional application No. 61/702,345, filed on Sep. 18, 2012.

(51) Int. Cl.

| | | |
|---|---|---|
| *C22B 3/26* | (2006.01) | |
| *C07C 29/76* | (2006.01) | |
| *C07C 51/47* | (2006.01) | |
| *C07C 67/56* | (2006.01) | |
| *C07D 207/06* | (2006.01) | |
| *C07D 333/76* | (2006.01) | |
| *C07F 9/09* | (2006.01) | |
| *C02F 101/10* | (2006.01) | |
| *C02F 101/20* | (2006.01) | |
| *C02F 101/30* | (2006.01) | |
| *C02F 103/10* | (2006.01) | |
| *C02F 103/24* | (2006.01) | |
| *C02F 103/30* | (2006.01) | |
| *C02F 103/32* | (2006.01) | |
| *C02F 101/34* | (2006.01) | |
| *C02F 103/34* | (2006.01) | |

(52) U.S. Cl.
CPC ............ *C07C 29/76* (2013.01); *C07C 51/47* (2013.01); *C07C 67/56* (2013.01); *C07D 207/06* (2013.01); *C07D 333/76* (2013.01); *C07F 9/09* (2013.01); *C22B 3/0005* (2013.01); *C02F 2101/103* (2013.01); *C02F 2101/20* (2013.01); *C02F 2101/308* (2013.01); *C02F 2101/34* (2013.01); *C02F 2103/10* (2013.01); *C02F 2103/24* (2013.01); *C02F 2103/30* (2013.01); *C02F 2103/325* (2013.01); *C02F 2103/343* (2013.01); *Y02P 10/234* (2015.11)

(58) Field of Classification Search
CPC ............ C02F 2101/308; C02F 2103/10; C02F 2103/24; C02F 2103/30; C02F 2103/325; C22B 3/0005
USPC ........................................................ 210/634
See application file for complete search history.

(56) References Cited

U.S. PATENT DOCUMENTS

| | | |
|---|---|---|
| 3,754,377 A | 8/1973 | Clonts |
| 3,758,404 A | 9/1973 | Clonts |
| 3,839,487 A | 10/1974 | Clonts |
| 3,977,829 A | 8/1976 | Clonts |
| 3,992,156 A | 11/1976 | Clonts |
| 4,130,549 A | 12/1978 | Ueno et al. |
| 4,266,026 A | 5/1981 | Breslau |
| 4,491,565 A | 1/1985 | Verachtert |
| 4,532,347 A | 7/1985 | Vaughan |
| 4,748,121 A | 5/1988 | Beaver et al. |
| 4,754,089 A | 6/1988 | Matson et al. |
| 4,992,200 A | 2/1991 | Lin et al. |
| 5,306,831 A | 4/1994 | Beshouri et al. |
| 5,523,426 A | 6/1996 | Jubin, Jr. et al. |
| 5,525,126 A | 6/1996 | Basu et al. |
| 5,578,090 A | 11/1996 | Bradin |
| 5,605,635 A | 2/1997 | David |
| 5,705,074 A | 1/1998 | Brient |
| 5,904,849 A | 5/1999 | Kim et al. |
| 5,997,731 A | 12/1999 | Suarez |
| 6,086,769 A | 7/2000 | Kilambi et al. |
| 6,127,560 A | 10/2000 | Stidham et al. |
| 6,132,491 A | 10/2000 | Wai et al. |
| 6,139,723 A | 10/2000 | Pelrine et al. |
| 6,174,501 B1 | 1/2001 | Noureddini |
| 6,214,232 B1 | 4/2001 | Baurmeister et al. |
| 6,238,566 B1 | 5/2001 | Yoshida et al. |
| 6,245,304 B1 | 6/2001 | Jansen et al. |
| 6,300,431 B1 | 10/2001 | Wang et al. |
| 6,303,830 B1 | 10/2001 | Argyropoulos et al. |
| 6,350,419 B1 | 2/2002 | Ho |
| 6,409,976 B1 | 6/2002 | Poschmann et al. |
| 6,887,304 B2 | 5/2005 | Stroh et al. |
| 7,112,229 B2 | 9/2006 | Khalil et al. |
| 7,153,996 B2 | 12/2006 | Fagan et al. |
| 7,207,445 B2 | 4/2007 | Manna et al. |
| 7,618,544 B2 | 11/2009 | Massingill, Jr. |
| 8,128,825 B2 | 3/2012 | Massingill |
| 9,168,469 B2 | 10/2015 | Massingill |
| 9,468,866 B2 | 10/2016 | Massingill |
| 2002/0003110 A1 | 1/2002 | Rohrbach et al. |
| 2003/0012715 A1 | 1/2003 | Bond et al. |
| 2003/0219366 A1 | 11/2003 | Horwitz et al. |
| 2004/0144712 A1 | 7/2004 | Stroh et al. |
| 2006/0008392 A1 | 1/2006 | Graham et al. |
| 2006/0042158 A1 | 3/2006 | Lee |
| 2007/0033863 A1 | 2/2007 | Butler |
| 2008/0300435 A1 | 12/2008 | Cortright et al. |
| 2010/0209982 A1 | 8/2010 | Basheer |

FOREIGN PATENT DOCUMENTS

| | | |
|---|---|---|
| CN | 101255348 | 9/2008 |
| EP | 0010466 | 4/1980 |
| EP | 0605173 | 7/1994 |
| EP | 1752770 | 2/2007 |
| EP | 2071015 | 6/2009 |
| EP | 2098553 | 9/2009 |
| EP | 2098556 | 9/2009 |
| GB | 2164663 | 3/1986 |
| WO | 88/04286 | 6/1988 |
| WO | 2004/110602 | 12/2004 |
| WO | 2011/110967 | 9/2011 |

OTHER PUBLICATIONS

Schlosser et al., "Recovery and separation of organic acids by membrane-based solvent extraction and pertraction: An overview with a case study on recovery of MPCA," Separation and Purification Technology, vol. 41, 2005, pp. 237-266.

Sabolova et al., "Liquid-Liquid Equilibria of Butyric Acid in Water + Solvent Systems with Trioctylamine as Extractant," J. Chem Eng. Data, vol. 46, 2001, pp. 735-745.

Schlosser et al., "Three-phase contactor with distributed U-shaped bundles of hollow-fibers for pertraction," Journal of Membrane Science, vol. 210, 2002, pp. 331-347.

Lazarova et al., "Application of large-scale hollow fiber membrane contactors for simultaneous extractive removal and stripping of penicilllin G," Journal of Membrane Science, vol. 202, 2002, pp. 151-164.

Earle et al., "Ionic liquids. Green solvents for the future," Pure Appl. Chem., vol. 72, No. 7, 2000, pp. 1391-1398.

"CRUD: How It Forms and Techniques for Controlling It," © 2006 Cytec Industries, Inc., 4 pages.

Davidson, "International Solvent Extraction Conference—ISEC 2011," Platinum Metals Review, vol. 56, Issue 3, Jul. 2012, pp. 177-180.

Garcia-Chavez et al., "Biobutanol Recovery Using Nonfluorinated Task-Specific Ionic Liquids," Ind. Eng. Chem. Res., vol. 24, 2012, pp. 8293-8301.

Sun et al., "Extraction separation of rare-earth ions via competitive ligand complexations between aqueous and ionic-liquid phases," Dalton Trans., vol. 40, 2011, pp. 8019-8023.

Zhang et al., "Physical Properties of Ionic Liquids: Database and Evaluation," J. Phys. Chem. Ref. Data, vol. 35, No. 4, 2006, pp. 1475-1517.

Wei et al., "Room temperature ionic liquid as a novel medium for liquid/liquid extraction of metal ions," Analytica Chimica Acta, vol. 488, 2003, pp. 183-192.

Makosza, "Phase-transfer catalysis. A general green methodology in organic synthesis," Pure Appl. Chem. vol. 72 No. 7, 2000, p. 1399-1403.

Office Action dated Sep. 14, 2015 for U.S. Appl. No. 14/030,760.

USE OF A FIBER CONDUIT CONTACTOR FOR EXTRACTION

PRIORITY CLAIM

This application is a continuation of pending U.S. patent application Ser. No. 14/030,760 filed on Sep. 13, 2013, which claims priority to U.S. Provisional Application No. 61/702,345 filed Sep. 18, 2012.

BACKGROUND OF THE INVENTION

1. Field of the Invention

This invention generally relates to fiber conduit reactors/contactors, and specifically relates to processes utilizing such devices to effect extraction from fluidic streams.

2. Description of the Related Art

The following descriptions and examples are not admitted to be prior art by virtue of their inclusion within this section.

Chemical extraction is desirable for a variety of reasons. In particular, many solids, liquids and gases contain contaminants which may hinder their further use and, thus, extraction of the contaminants is desirable. In addition or alternatively, many solids, liquids and gases contain valuable substances which are desirable to extract. Moreover, waste streams often contain pollutants which do not meet environmental regulations. As such, considerable effort and expense is often undertaken to remove the chemical species from fluidic streams and solids. Examples of chemical species that are often extracted from fluid streams and solids include but are not limited to dyes, acids, bases, phenolics, amines, sulfur compounds, solvents, catalysts, drugs, and heavy metals, etc. As a particular example, hydrodesulfurization is often used to desulfurize petroleum streams contaminated with sulfur containing compounds, but the process is relatively expensive and dangerous as it is conducted at high temperatures and pressures.

One manner of chemical extraction involves dispersions of one fluidic phase in another to generate small droplets with a large surface area where mass transfer and reaction can occur. In cases of solvent extraction, one or more chemical agents are used to break down the components within a substance to enable extraction. Those materials which are more soluble or react more readily to a particular acid or base get separated from the rest. The separated materials are then removed, and the process begins all over again with the introduction of more chemicals to leach out more components. In any case, the time required for solvent extraction can vary widely. In particular, some materials need to be allowed to mix and sit for a long period of time for the components to separate out. Complicating things further is that many of the chemicals used as well as some by-products of solvent extraction are extremely hazardous and must be handled and disposed of with great care.

A common method of recovering metals from ores and concentrates is by leaching with a mineral acid. The leached liquid containing the dissolved metal, known as a pregnant leach solution, is collected and further processed to extract and separate the metals. By way of example, rare earth metals are generally recovered from bastnaesite by leaching the host rock with hydrochloric acid. Uranium can be recovered from uranium-containing host rock by leaching with phosphoric acid. Copper, beryllium, nickel, iron, lead, molybdenum, aluminum, and manganese can be recovered from host rock by leaching with nitric acid. Copper, beryllium, nickel, iron, lead, molybdenum, aluminum, germanium, uranium, gold, silver, cobalt, and manganese can be recovered from host rock by leaching with sulfuric acid or hydrochloric acid. In hydrometallurgy, mineral concentrates are separated into usable oxides and metals through liquid processes, including leaching, extraction, stripping, and precipitation. By these means, the elements are dissolved and purified into leach solutions. The metal or one of its pure compounds (such as an oxide) is then precipitated from the leach solution by chemical or electrolytic means. In stripping, the metal in the organic solution is stripped (extracted) by an acidic solution to form a loaded strip liquor (loaded electrolyte), resulting in a much purer metal solution. If the volume of the strip solution is much smaller than that of the organic solution, metal is also concentrated.

Mining metal compounds is relatively simple, but extracting individual elements from the ore can sometimes be difficult. For example, processing of rare earth elements and metals of the precious metal group and the uranium group as well as many other metals often requires dozens of procedures each resulting in minute changes in the complex stream. In many cases the procedures need to be repeated, and thus, separating and extracting a single metal element, especially one of the heavy metal elements, takes a great deal of time, effort and expertise. Furthermore, the complex metallurgical technologies have taken decades to evolve, and each metal element presents its own unique challenges for separating and extracting. As a result, it can take many years for scientists to crack the geological code and design appropriate metallurgic processes for each metal element stream.

A common method of recovering volatile products from solutions involves distillation of the product from the solution. For instance, alcohols are often produced by fermentation and recovered by energy intensive distillation. Another method of recovering chemicals from aqueous or other production streams involves adsorption and desorption from solids, but such processes are often laborious, expensive, and/or produce undesirable waste. For example, pollutants from effluent air streams are frequently processed using solid adsorbants. Another example is adjusting a fermentation broth containing valuable pharmaceutical product through a series of pH changes, passing it through either a silica or a polymeric chromatography packing, and subsequently using reverse phase column chromatography to produce products from an adsorbent resin. After repeating the process a salt of the product is crystallized with a solvent and the crystals are neutralized and the product is precipitated in an organic solvent such as acetone or alcohol to produce pure product.

An undesirable byproduct of many extraction processes is the formation of a gelatinous emulsion of chemical phases (often organic and aqueous phases) known as crud, gunk, grungies, grumos, or a rag layer. Problems can occur as the amount of crud builds up in the system, particularly hindering a system's ability to reduce operational costs and in cases of excessive crud formation (or poor crud management), crud can also impact production. Since it is difficult to avoid the formation of crud, most operations have systems for removing it. A further disadvantage of the formation of crud is that once it is removed from a system it must be treated so that the solvent used to extract the noted chemical can be recovered. Techniques vary at different operations, but all include some basic physical force used to separate the solid and liquid phases of crud, such as a centrifuge, filter press, or agitated tank. When choosing a treatment method, one has to consider the economics associated with stopping production to remove crud, as opposed to processing the crud while the plant is in operation.

Accordingly, it would be desirable to develop different systems and methods for efficiently and cost-effectively extracting chemicals from fluids and solids, particularly systems and methods of reduced complexity and which minimize waste.

SUMMARY OF THE INVENTION

Processes are provided which utilize fiber conduit reactors/contactors to effect extraction from a fluid stream, particularly a fermentation broth, a waste stream of a fermentation process, a fluid comprising a dye, or a fluid comprising a pharmaceutical compound. In particular, methods are provided which include introducing a first stream comprising an extractant proximate a plurality of fibers positioned within a conduit reactor and extending proximate to one or more collection vessels. The method further includes introducing a second stream into the conduit reactor proximate to the plurality of fibers, wherein the second stream is in contact with and is substantially immiscible with the first stream. The first stream and the second stream are introduced into the conduit reactor such that the extractant of the first stream interacts with the second stream to extract a fermentation product, a fermentation byproduct, a dye or a pharmaceutical compound from the second stream into the first stream. The method further includes receiving the first and second streams in the one or more collection vessels and withdrawing separately the first and second streams from the one or more collection vessels.

BRIEF DESCRIPTION OF THE DRAWINGS

For a more complete understanding of the present invention, and the advantages thereof, reference is now made to the following descriptions taken in conjunction with the accompanying drawings, in which.

Figure 1:
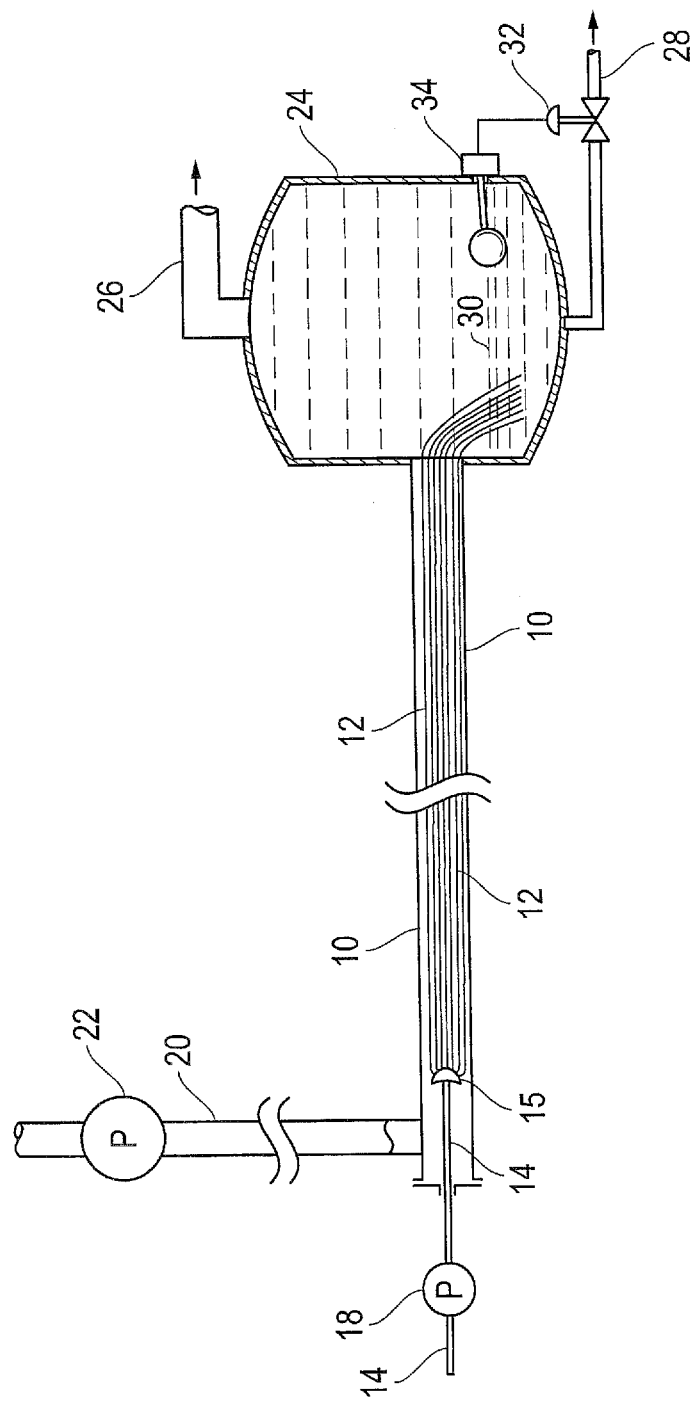
FIG. 1 illustrates an example of a fiber conduit contactor useful for the processes described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The disclosure herein relates generally to fiber conduit reactors/contactors, and specifically to processes utilizing such devices to effect separation and reaction between two immiscible reaction components using catalysts, solvents, and/or co-solvents. More specifically, the disclosure herein is directed to new and improved processes for extraction of chemical compounds and/or chemical elements of a first fluid by component(s) of a second, substantially immiscible fluid in a fiber conduit reactor/contactor. Applications of particular interest include extraction of metal compounds and metal elements from fluid streams, but extraction of various metalloid and non-metal compounds as well as various metalloid and non-metal elements from fluid streams are disclosed as well. As used herein, the term "element" refers to a substance consisting of only one type of atom. In contrast, the term "compound," as used herein, refers to a material formed from two or more different elements that are chemically combined (i.e., the atoms are held together by chemical bonds) in definite proportions by mass. Both elements and compounds are categorized herein as "pure chemical substances" in that they cannot be broken down into individual components by a physical change. This categorization differs from that of a "chemical mixture," which is referred to herein as a combination of two or more pure chemical substances that can be separated by a physical change (i.e., the pure chemical substances of a mixture are not combined by chemical bonds).

As set forth in more detail below, the processes described herein may be particularly applicable for processes associated with mining. Other applications, however, are disclosed as well, including but not limited to processes used to produce a concentrated or purified product in one of the process streams. For example, applications of the processes described herein may alternatively include extraction of metal elements or metal compounds from manufacturing, refinery or waste streams of processes other than those associated with mining. Yet other applications may include extraction of fermentation products or byproducts from manufacturing or waste streams, such as for example extraction of alcohols or acids from fermentation broths or fermentation waste streams. In some cases, applications of the processes disclosed herein may include removing pollutants, contaminants, and/or impurities from process or waste streams, such as but not limited to extracting organosulfur compounds from petroleum streams or extracting diacetin, monoacetin and/or glycerol from biodiesel-triacetin mixtures. Furthermore, processes for extracting dyes from fluid streams and processes for extracting pollutants from gas streams, such as sulfur compounds, $CO_2$, CO, $NO_x$ from air or natural gas, are provided.

Applications are also disclosed involving the extraction of neutraceutical compounds and/or elements (e.g., ib and/or minerals) from fluid streams and the extraction of pharmaceutical compounds (e.g., ibuprofen or antibiotics (such as Trimethoprim) from production fluids (a.k.a., manufacturing broths)). Another process described herein which may be particularly applicable but is not necessarily limited to the pharmaceutical field is the extraction of enantiopure compounds from a fluid stream. In some embodiments, the extraction processes described herein may be used to separate water soluble entities from aqueous acid or aqueous alcohol manufacturing or refinery product streams (e.g., streams containing ethanol, butanol, acetic acid, lactic acid, pyruvic acid, picolinic acid, 1,2-propanediol, and the like) or vice versa to dehydrate them without distillation. In further embodiments, the extraction processes may be used to extract solvents and/or catalysts from a fluid stream. Other applications may be suitable as well.

As noted above, extraction processes may be conducted in a fiber conduit reactor to extract metals from fluids, such as leachates or other fluids. Examples of metals which may be extracted from fluids include alkali metals (i.e., lithium, sodium, potassium, rubidium, cesium, and francium); alkaline earth metals (i.e., beryllium, magnesium, calcium, strontium, barium, and radium); transition metals (i.e., zinc, molybdenum, cadmium, scandium, titanium, vanadium, chromium, manganese, iron, cobalt, nickel, copper, yttrium, zirconium, niobium, technetium, ruthenium, rhodium, palladium, silver, hafnium, tantalum, tungsten, rhenium, osmium, iridium, platinum, gold, mercury, rutherfordium, dubnium, seaborgium, bohrium, hassium, and copernicium); post-transition metals (i.e., aluminum, gallium, indium, tin, thallium, lead, bismuth, and polonium); lanthanides (i.e., lanthanum, cerium, praseodymium, neodymium, promethium, samarium, europium, gadolinium, terbium, dysprosium, holmium, erbium, thulium, ytterbium, and lutetium); actinides (i.e., actinium, thorium, protactinium, uranium, neptunium, plutonium, americium, curium, berkelium, californium, einsteinium, fermium, mendelevium, nobelium, and lawrencium); elements which are possibly metals (e.g., meitnerium, darmstadtium, roentgenium, ununtrium, flerovium, ununpentium, and livermorium); and elements which are sometimes considered metals (i.e., metalloids, e.g., germanium, arsenic, antimony, and astatine). It is noted that other classification of metal groups may be considered for the processes described herein. For example, the processes described herein may be used to extract precious metals (e.g., platinum, rhodium, gold, iridium, osmium, palladium, rhenium, ruthenium or silver).

In some cases, the extraction processes described herein (i.e., processing through a fiber conduit reactor) may be particularly suited to extracting rare earth elements (REEs). In particular, because REEs are so similar in chemical behavior, they are difficult to separate from each other and, thus, conventional extraction methods require multiple stages to complete the extraction process. The processes described herein, however, have a high rate of mass transfer, and, thus REEs may be extracted out of solution faster than conventional techniques. As such, the processes may be used to extract one or more REEs from streams, including those which do not include other metals and those which do. In some cases, the processes described herein may be used to extract an REE from other REEs. In addition or alternatively, other metals may be extracted using the fiber conduit reactor described herein.

In some cases, an extractant solution discharged from a fiber conduit reactor may include more than one metal. In such embodiments, the metals may be selectively recovered (scrubbed) from the extractant solution by washing the solution with strong aqueous acids. Such a washing process may be conducted in a fiber conduit reactor or alternatively may be conducted by another technique. In yet other cases, metals may be selectively extracted from a fluid in a single extraction pass through a fiber conduit reactor by using two extraction solvents simultaneously within the reactor as described in more detail below. In particular, the processes described herein (i.e., processes conducted through a fiber conduit reactor) may be applicable for extracting one or more metals from solutions containing more than one metal. For example, the processes may be conducted in a fiber conduit reactor to extract copper from zinc; gold, silver, platinum, palladium from other metals and/or from each other; transuranium metals from other metals and/or each other; heavy metals from drinking water and/or process water.

The fiber conduit apparatuses used to employ the processes described herein may be utilized as reactors, extractors and/or contactors. For simplicity, the fiber conduit apparatuses considered for the processes described herein are interchangeably referred to as fiber conduit contactors, fiber conduit reactors, fiber conduit receivers, fiber conduit contactors/reactors and/or fiber conduit contactors/reactors/receivers. It is noted that some extraction processes involve a chemical reaction to affect extraction while others may not. Embodiments of fiber conduit reactors which may be employed for the methods discussed herein are shown and described in U.S. Pat. Nos. 3,754,377; 3,758,404; 3,992,156; 4,491,565; 7,618,544; and 8,128,825, all which are incorporated herein by reference to the extent not inconsistent herewith. In general, the processes described herein employ two essentially immiscible fluids with reactive components in them, including one phase which preferentially wets the fibers of the conduit reactor (hereinafter referred to as the "constrained phase") and another phase which is passed between the fibers (hereinafter referred to as the "continuous phase"). Depending on the process employed, a catalyst, solvent or cosolvent may also be used within the fiber conduit reactor. In any case, the phases discharged from the fiber conduit reactor may be separately withdrawn and, in some cases, either or both phases may be further processed in the same fiber conduit reactor, a different fiber conduit reactor, or another processing apparatus, such as for washing, separation and/or further extraction.

Advantages of using a fiber conduit reactor for extracting, separating, reacting and/or contacting elements and compounds include but are not limited to:
(1) Processes are very fast because of very high surface area for mass transfer.
(2) Faster processing allows relatively small fiber conduit reactors to be used instead of large open settling zones and/or tanks. As a result, the footprint of the process, the cost and size of the process equipment, and loss of volatile organics will be less, with significant implications for solvent recovery rates and plant safety.
(3) By-products are greatly reduced because dispersions and rag layers (crud) are virtually eliminated. Since dispersions are reduced and sometimes eliminated, settling time for coalescence of the dispersed particles is reduced and sometimes eliminated, thus reducing collection and processing time and costs, which give way to an even smaller plant foot print.
(4) The conduit reactor is an extremely effective microchannel extractor/reactor/contactor with the additional benefit of being easily scaled up to any desired volume by simply using larger diameter conduits with more fibers. This is in stark contrast to other traditional "scale-up" approaches, where larger volumes can impact the physical processes and efficiencies involved.

As previously mentioned, an undesirable byproduct of many extraction processes, particularly bulk processing, is the formation of a gelatinous emulsion of chemical phases (often organic and aqueous phases) known as crud, gunk, grungies, grumos, or a rag layer. In general, crud is formed by the diffusion of particles, particularly nanoparticles, into the liquid-liquid interface of the two immiscible liquids used in the extraction process. The behavior of nanoparticles in processes performed in a fiber conduit reactor, however, differs greatly from processes performed in bulk processing. The main difference between the two methods is the type of flow. In bulk processing, the turbulent mixing of the two phases promotes transport of particles to the liquid-liquid interface. In contrast, free phase flow in the fiber conduit reactor is laminar so that transport of particles to the liquid-liquid interface is much slower, often slower than the diffusion, complexation and extraction rates of ions at the liquid-liquid interface. For example, the typical diffusion time of metal ions to a liquid-liquid interface via solvent extraction is about 6 seconds and then the complexation and extraction of the metal ions takes about another minute to reach equilibrium. In contrast, the diffusion time of silica particles in solution, for example, is typically more than one hour (i.e., depending on the viscosity and fluid dynamics of the solution as well as particle size). Thus, if the contact time between immiscible liquids in a fiber conduit contactor/reactor is designed to be shorter than the characteristic diffusion time of particles in the liquids, the crud problem in a fiber conduit contactor/reactor may be avoided.

The fibers employed in a fiber conduit reactor for the extraction processes described herein may, in some cases, be longitudinal and extend substantially parallel to the sidewalls of the reactor conduit. Other fiber configurations, however, may be considered. In particular, in some embodiments, the fibers may be arranged off angle relative to the conduit sidewalls (i.e., not parallel) (e.g., the fibers may extend from an off-center location at top of the pipe to the bottom center or to a bottom opposing sidewall or vice versa, etc.). In addition or alternatively, the fibers may be crimped (i.e., zig zag), spiral wound, and/or intertwined (e.g., similar to steel wool cleaning pads stuffed in a pipe). In some embodiments, the fibers may have a circular cross-section, but other cross-sectional shapes may be considered, such as but not limited to elliptical, triangular, square, rectangular, dog-bone, bean-shaped, multi-lobular, and polygonal. In some cases, the fibers may be scaled or serrated. In other embodiments, the exterior surfaces of the fibers may be smooth. In some cases, the fibers can be threads made of relatively short fibers twisted together. In other embodiments, the fibers may be configured similar to a treelike structure with a main fiber and various size limbs and branches attached to the main trunk. Multifilament fibers (textile threads) and less symmetrical monofilaments have greater possibility for dispersions created in the exiting free phase, so it would be preferable to use symmetrical monofilament fibers, but reaction/extraction still occurs using multifilament non-symmetrical fibers and the resulting dispersion may be generally manageable in practice. In any case, the configuration of the fibers (e.g., shape, size, number of filaments comprising a fiber, symmetry, asymmetry, etc.) within a conduit reactor may be the same or different for the processes described herein.

The material of fibers for the extraction processes described herein may be, but are not limited to, cotton, jute, silk, treated or untreated minerals, metals, metal alloys, treated and untreated carbon allotropes, polymers, polymer blends, polymer composites, nanoparticle reinforced polymer, combinations thereof, and coated fibers thereof for corrosion resistance or chemical activity. In general, the fiber type is selected to match the desired constrained phase. For example, organophilic fibers may be used with a constrained phase that is substantially organic. This arrangement can, for example, be used to extract organic materials from water with organic liquids constrained to the fibers. Suitable treated or untreated minerals include, but are not limited to, glass, alkali resistant glass, E-CR glass, quartz, asbestos, ceramic, basalt, combinations thereof, and coated fibers thereof for corrosion resistance or chemical activity. Suitable metals include, but are not limited to, iron, steel, stainless steel, nickel, copper, brass, lead, thallium, bismuth, indium, tin, zinc, cobalt, titanium, tungsten, nichrome, zirconium, chromium, vanadium, manganese, molybdenum, cadmium, tantalum, aluminum, anodized aluminum, magnesium, silver, gold, platinum, palladium, iridium, alloys thereof, and coated metals.

Suitable polymers include, but are not limited to, hydrophilic polymers, polar polymers, hydrophilic copolymers, polar copolymers, hydrophobic polymers/copolymers, non-polar polymers/copolymers, and combinations thereof, such as polysaccharides, polypeptides, polyacrylic acid, polyhydroxybutyrate, polymethacrylic acid, functionalized polystyrene (including but not limited to, sulfonated polystyrene and aminated polystyrene), nylon, polybenzimidazole, polyvinylidenedinitrile, polyvinylidene chloride and fluoride, polyphenylene sulfide, polyphenylene sulfone, polyethersulfone, polymelamine, polyvinyl chloride, polyvinylacetate, polyvinylalcohol, co-polyethylene-acrylic acid, polyethylene terephthalate, ethylene-vinyl alcohol copolymers, polyethylene, polychloroethylene, polypropylene, polybutadiene, polystyrene, polyphenol-formaldehyde, polyurea-formaldhyde, polynovolac, polycarbonate, polynorbornene, polyfluoroethylene, polyfluorochloroethylene, polyepoxy, polyepoxyvinylester, polyepoxynovolacvinylester, polyimide, polycyanurates, silicone, liquid crystal polymers, derivatives, composites, nanoparticle reinforced, and the like.

In some cases, fibers can be treated for wetting with preferred phases, to protect from corrosion by the process streams, and/or coated with a functional polymer. For instance, carbon fibers can be oxidized to improve wettability in aqueous streams and polymer fibers can display improved wettability in aqueous streams and/or be protected from corrosion by incorporation of sufficient functionality into the polymer, including but not limited to, hydroxyl, amino, acid, base, enzyme, or ether functionalities. In some cases, the fibers may include a chemical bound (i.e., immobilized) thereon to offer such functionalities. In some embodiments, the fibers may be ion exchange resins, including those suitable for hydroxyl, amino, acid, base or ether functionalities. In other cases, glass and other fibers can be coated with acid, base, or ionic liquid functional polymer. As an example, carbon or cotton fibers coated with an acid resistant polymer may be applicable for processing strong acid solutions. In some cases, fibers may include materials that are catalytic or extractive for particular processes. In some cases, the enzymatic catalysts may comprise the fibers to aid in particular reactions and/or extractions.

In some embodiments, all the fibers within a conduit reactor may be of the same material (i.e., have same core material and, if applicable, the same coating). In other cases, the fibers within a conduit reactor may include different types of materials. For example, a conduit reactor may include a set of polar fibers and a set of non-polar fibers. Other sets of varying materials for fibers may be considered. As noted above, the configuration of fibers (e.g., shape, size, number of filaments comprising a fiber, symmetry, asymmetry, etc.) within a conduit reactor may be the same or different for the processes described herein. Such variability in configuration may be in addition or alternative to a variation of materials among the fibers. In some embodiments, different types of fibers (i.e., fibers of different configurations and/or materials) may run side by side within a reactor with each set having their own respective inlet and/or outlet. In other cases, the different types of fibers may extend between the same inlet and outlet. In either embodiment the different types of fibers may be individually dispersed in the conduit reactor/contactor or, alternatively, each of the different fiber types may be arranged together. In any case, the use of different types of fibers may facilitate multiple separations, extractions, and/or reactions to be performed simultaneously in a conduit reactor from a singular or even a plural of continuous phase streams. For example, in a case in which a conduit reactor/contactor is filled with multiple bundles of respectively different fiber types each connected to its own constrained phase fluid inlet and arranged off-angle, the bundles could be arranged for the continuous phase fluid to pass sequentially over the multiple fiber bundles with different materials extracted by or from each bundle.

The constrained phase of a process conducted in a fiber conduit reactor can include any liquid that wets the fibers preferentially to the continuous phase, including but not limited to, such materials as organophosphorus acids, water, water solutions, water and co-solvents, alcohols, phenols, amines (including but not limited to, polyamines, ethanolamines, and polyethanolamines), carboxylic acids, ethers, esters, dimethyl sulfoxide, sulfone, dimethyl formamide, ketones, aldehydes, saturated and unsaturated aliphatic hydrocarbons, aromatic hydrocarbons, silicone containing fluids, halogenated solvents, liquefied gases, sulfuric acid, other mineral acids, liquid metals/alloys, and ionic liquids. The scope of the ionic liquids which may be utilized in the methods described herein is set forth in detail below. The continuous phase of a process conducted in a fiber conduit reactor can include any liquid immiscible with the selected constrained phase. Immiscible ionic liquids for example can be used together, one as a constrained phase and one as a continuous phase.

For extraction processes, the constrained phase frequently comprises the extractant, but functionalities of the constrained phase and the continuous phase can be reversed if desired by reversing the polarity of the fibers chosen for a particular separation. In some cases, a solvent may be the extractant. In other embodiments, an extractant may be mixed with a solvent (i.e., the solvent may be used as a carrier medium for the extractant). In either case, extractant is frequently diluted in another solvent. Examples of diluted extractants which may be used for some processes include but are not limited to Ionquest-801 (an organophosphorus acid) diluted in an aliphatic organic compound; 1-phenyl-3-methyl-4-benzoly-5-pyrazolone (HPMBP) as the extractant in aqueous-chloroform; D2EHPA, acetylacetone and 1,10-phenanthroline in non-polar organic solvents. In some embodiments, the phase used for extraction may include two immiscible liquids to affect selective extraction for multiple entities. For instance, a continuous phase of two immiscible liquids may be used to extract different metals from a fluid stream in the constrained phase or vice versa. Such a process may be advantageous to avoid having to process (i.e., wash) an extractant solution discharged from a fiber conduit reactor. In some cases, two immiscible ionic liquids may be used to affect selective extraction of entities, such as different metals.

The term ionic liquid (IL) is used herein to refer to a salt in a liquid state. In some cases, the term is specific to salts having a melting point below 100° C. ILs are also known as liquid electrolytes, ionic melts, ionic fluids, or liquid salts. An advantage of ILs is their high solvation ability for compounds of widely varying polarity. Furthermore, utilizing ILs is one of the goals of green chemistry because ILs potentially create a cleaner and more sustainable chemistry as environmental friendly solvents for many extractive, reactive, and catalytic processes. Moreover, utilizing ILs offer potential improvement in process economics, chemical reactivity, selectivity, and yield. As such, it may be particularly advantageous, in some cases, to employ ionic liquids for the processes described herein.

A specific category of ionic liquids are room temperature ionic liquids (RTILs), which are salts having a melting point at or below room temperature (i.e., at or below 20° C.). RTILs have advantages over conventional organic diluents, such as negligible vapor pressure, low flammability, moisture stability, relatively high radiation stability, different extraction properties and a possibility of eliminating aqueous phase acidification. Furthermore, it has been demonstrated that extraction efficiency of RTIL can be modulated by a chelating agent. For example: 1) highly efficient extraction of strontium ions can be achieved when dicyclohexane-18-crown-6 (DC18C6) is combined with RTILs; 2) the extraction of various alkali metal ions can be achieved with crown ethers in RTILs; 3) octyl(phenyl)-N,N-diisobutylcarbamoylmethyl-phosphine oxide dissolved in RTILs enhanced the extractability of lanthanides and actinides in comparison to conventional organic solvents; 4) the extraction of silver ions is greatly enhanced by a combined application of RTIL and calyx[4]arene compared to that of chloroform; 5) task-specific RTILs with coordination capacity built in the RTIL cation have been reported; and 6) increased efficiency has been shown of chelate extraction of 3d-cations like Cs with 8-sulfonamidoquinoline, Pu(IV) with carbamoylmethylphosphine oxide, and uranyl ion with tributylphosphate. As such, it may be particularly advantageous, in some cases, to employ RTILs for the processes described herein. As an example, the aforementioned embodiments of metal extraction using RTILs may be performed in a fiber conduit reactor.

ILs are usually formed by a large organic cation combined with an anion of smaller size and more symmetrical shape, although some symmetric cations are also combined with asymmetric anions to form ionic liquids. In spite of their strong charges, their asymmetry prevents them from solidifying at low temperatures. Furthermore, ionic liquids can be made hydrophilic or hydrophobic. Some common cations which may be considered for the formation of ILs employed herein are imidazolium, benzotriazolium, pyrrolidinium, piperidinium, pyridinium, isoquinolinium, thiazolium, sulfonium, ammonium, phosphonium and aminium, but other cations may be considered. Some common anions which may be considered for the formation of ILs employed herein are halide, borate, carbon icosahedral, nitrite, amides, imides, nitrate, hydrofluoride anions, aluminate, mesylate, sulfate, sulfinates, sulfonates, tosylate, sulfate, phosphate, acetate, alkanoates, aluminate, arsenic, niobium, tantalum and trisubstitued methane, but other anions may be considered. In particular, a comprehensive database from literature date between 1980 and 2004 has been published denoting 276 kinds of cations and 55 kinds of anions suitable for IL formation ("Physical Properties of Ionic Liquids: Database and Evaluation," J. Phys. Chem. Ref. Data, Vol. 35, No. 4, 2006).

ILs are advantageous because they can be tuned with a well-judged selection of the cation-anion pair, giving the opportunity to choose among a vast range of different ionic liquids. In particular, hundreds of ionic liquids have been synthesized and there is virtually no limit in the number of possible counter-ion pairs and mixtures of them that can be obtained. In fact, the number of possible ionic liquids is estimated around $10^{18}$, whereas the number of traditional solvents widely used in industry is only a few hundred. ILs based on a specific organic cation and/or anion for several potential specific applications are known, examples of which include chiral ionic liquids (using natural or synthesized chiral units) for asymmetric catalytic transformations, enantioselective resolution or separation processes; pharmaceutical ionic liquids (called API-ILs incorporating an active principle ingredient as cation or anion); magnetic ionic liquids (based on FeCl4 anions) for efficient separation processes; and as intrinsically functional materials (for example luminescent, photochemical or electrochemical ILs).

In addition, IL compounds can also be tuned by the modification of the cation and/or the anion molecular structure adding appropriate functional groups in order to obtain ionic liquids with a set of desired physico-chemical properties, which are known as task specific ionic liquids (TSIL). In particular, supramolecular structure and organization have emerged as important and complicated topics that may be key to understanding how chemical reactions and other processes are affected by ionic liquids. In general, TSILs may be developed with desired physico-chemical properties such as density, thermal/electrical conductivity, viscosity, polarity, and non-toxic or biodegradable ILs. For example, protic ILs generally have stronger polarities and can dissolve metal salts to a greater extent than common aprotic ILs. These protic ILs have been utilized in the electrodeposition of silver and zinc. As another example, N-alkylethylenediamines have two amines and are more favorable for an incorporation of Lewis acids such as proton and transition metal ions into the ILs in comparison with N-alkylamines.

In addition to the above parameters for varying properties, it has also been reported that replacing one atomic element in an ionic species with another heavier element affects the physical and chemical properties of ILs in unexpected ways. For instance, comparison of ILs with C and Si in a side group of 1-methyl-3-neopentylimidazolium and 1-methyl-3-trimethylsilyl-methyl-imidazolium with the same anion showed that shear viscosities of the silicon substituted ILs were substantially less than those of the respective carbon ILs. Heavy atom substitution also affects the static properties such as liquid density, shear viscosity, and surface tension. This feature of ILs is the opposite of that observed in conventional neutral molecular liquids.

Computer modeling tools are being developed that will enable ILs to be designed for specific tasks. Two different and complementary approaches have shown excellent predictive power: (1) the soft-SAFT equation of state, used to predict the solubility of several compounds in different families of alkylimidazolium ionic liquids, as well as interfacial properties, and (2) classical molecular dynamic simulations, used to study transport properties like self-diffusion, viscosity and electrical conductivity of ionic liquids. These tools help in getting additional insights into the underlying mechanisms governing the behavior of these systems, which is the basic knowledge needed for a rational design of TSILs. It is noted that TSILs may be advantageous for any of the applications disclosed herein.

Turning to FIG. 1, which depicts a fiber conduit reactor similar to the one disclosed in U.S. Pat. No. 3,977,829, conduit 10 has a bundle of elongated fibers 12 filling conduit 10 for a portion of its length. Fibers 12 are secured to tube 14 at node 15. Tube 14 extends beyond one end of conduit 10 and has operatively associated with its metering pump 18 which pumps a first (constrained) phase liquid through tube 14 and onto fibers 12. Operatively connected to conduit 10 upstream of node 15 is inlet pipe 20 having operatively associated with it metering pump 22. This pump 22 supplies a second (continuous) phase liquid through inlet pipe 20 and into conduit 10, where it is squeezed between the constrained coated fibers 12. At the downstream end of conduit 10 is gravity separator or settling tank 24 into which the downstream end of fibers 12 may extend. Operatively associated with an upper portion of gravity separator 24 is outlet line 26 for outlet of one of the liquids, and operatively associated with a lower portion of gravity separator 24 is outlet line 28 for outlet of the other liquid, with the level of interface 30 existing between the two liquids being controlled by valve 32, operatively associated with outlet line 28 and adapted to act in response to a liquid level controller indicated generally by numeral 34.

Although the fiber conduit contactor shown in FIG. 1 is arranged such that fluid flow traverses in a horizontal manner, the arrangement of the fiber conduit contactor is not so limited. In particular, in some cases, the fiber conduit contactor may be arranged such that inlet pipes 14 and 20 as well as node 15 occupies an upper portion of the apparatus and settling tank 24 occupies the bottom portion of the apparatus. For example, the fiber conduit contactor shown in FIG. 1 may be rotated approximately 90° in parallel with the plane of the paper to arrange inlet pipes 14 and 20, node 15 and settling tank 24 in the noted upper and lower positions. Such an arrangement may capitalize on gravity forces to aid in propelling fluid through the reactor. In yet other embodiments, the fiber conduit contactor depicted in FIG. 1 may be rotated approximately 90° in the opposite direction parallel with the plane of the paper such that inlet pipes 14 and 20 and node 15 occupies the bottom portion of the apparatus and settling tank 24 occupies the upper portion of the apparatus. In such cases, it was discovered that the hydrophilicity, surface tension, and repulsion of the continuous phase fluid will keep the constrained phase fluid constrained to the fibers regardless of whether the fluids are flowing up, down, or sideways and, thus, sufficient contact can be attained to effect the desired reaction and/or extraction without the need to counter gravity forces. It is noted that such an inverted arrangement of a fiber conduit contactor is applicable for any of the extraction processes described herein as well as any other type of fluid contact process that may be performed in a fiber conduit contactor/reactor. It is further noted that fiber conduit contactors may be arranged in a slanted position for any of the extraction processes described herein or for any other process that may be performed in a fiber conduit contactor/reactor (i.e., the sidewalls of the fiber conduit contactor may be arranged at any angle between 0° and 90° relative to a floor of a room in which the fiber conduit contactor is arranged).

Figure 2:
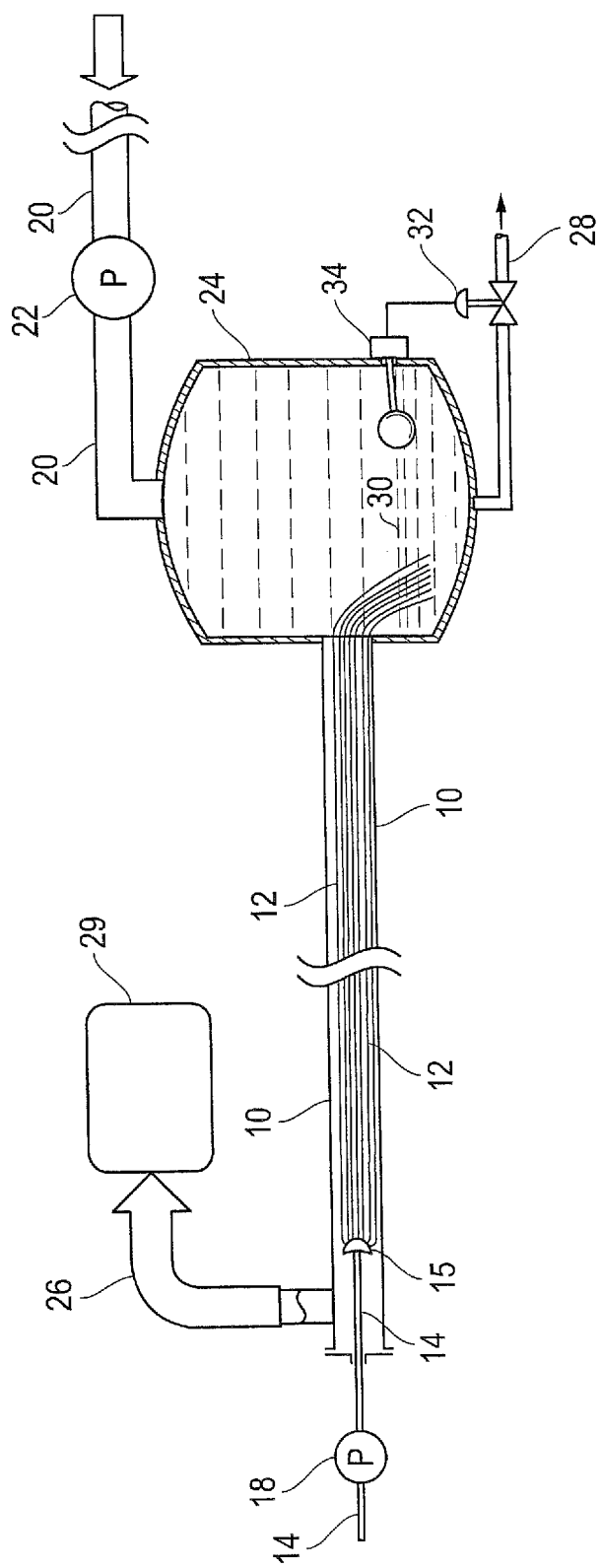
FIG. 2 illustrates an example of another fiber conduit contactor useful for the processes described herein.

In an alternative embodiment, a counter-current fiber conduit contactor/reactor may be used for the methods described herein. An example of a counter-current fiber conduit contactor/reactor is illustrated in FIG. 2. In particular, FIG. 2 illustrates an alternative configuration of the fiber conduit contactor/reactor depicted in FIG. 1, specifically that the locations of inlet pipe 20 and associated pump 22 have been switched with outlet line 26 to affect counter-current flow of the continuous phase relative to the flow of the constrained phase in conduit 10. Similar to the fiber conduit contactor/reactor depicted in FIG. 1, the fiber conduit contactor/reactor depicted in FIG. 2 includes conduit 10 having a bundle of elongated fibers 12 secured to tube 14 at node 15 and extending a portion of the length of conduit 10. Tube 14 extends beyond one end of conduit 10 and has operatively associated with its metering pump 18 which pumps a first (constrained) phase liquid through tube 14 and onto fibers 12. At the other end of conduit 10 is settling tank 24 into which fibers 12 extend and unload the first phase liquid.

Outlet line 28 is arranged at a lower portion of settling tank 24 for discharge of the first phase liquid as controlled by valve 32, which operates in response to level monitor 34 arranged at interface 30.

As noted above, the fiber conduit contactor/reactor/receiver depicted in FIG. 2 differs from the one depicted in FIG. 1 by the locations of inlet pipe 20 and associated pump 22 have been switched with outlet line 26. In particular, inlet pipe 20 and associated pump 22 in FIG. 2 are connected to an upper portion of settling tank 24 to introduce a second (continuous) phase liquid into settling tank 24 and conduit 10, where it is squeezed between the fibers 12 coated with the first constrained phase liquid. In addition, the fiber conduit contactor/reactor depicted in FIG. 2 includes outlet 26 for the discharge of the second continuous phase liquid from conduit 10 into collection tank 29. An optional addendum to the fiber conduit contactor configuration depicted in FIG. 2 would be to add an extension line from pipe 20 to conduit 10 near its port to settling tank 24. Such an additional extension line may be used to feed the second (continuous) phase liquid into conduit 10 while bypassing settling tank 24. In any case, due to the configuration of the contactor/reactor/receiver depicted in FIG. 2, the size of its settling tank 24 may be optionally reduced by up to 50% relative to the size used for the fiber conduit contactor/reactor/receiver depicted in FIG. 1

In any case, with the counter-current fiber conduit contactor configuration depicted in FIG. 2, it was discovered that the hydrophilicity, surface tension, and repulsion of the continuous liquid phase will keep the constrained phase liquid constrained to the fibers even when the constrained phase liquid is flowing in the opposite direction. Such a phenomenon is true in cases in which the constrained phase liquid is flowing up, down, or sideways and, thus, although the counter-current fiber conduit contactor shown in FIG. 2 is arranged such that fluid flow traverses in a horizontal manner, the arrangement of the fiber conduit contactor is not so limited. In particular, the counter-current fiber conduit contactor shown in FIG. 2 may be rotated approximately 90° in either direction parallel with the plane of the paper to respectively arrange inlet pipe 14 and settling tank 24 in upper and lower positions of the apparatus or vice versa. In yet other embodiments, the fiber conduit contactor depicted in FIG. 2 may be arranged in a slanted position (i.e., the sidewalls of the fiber conduit contactor may be arranged at any angle between 0° and 90° relative to a floor of a room in which the fiber conduit contactor is arranged). In any case, the counter-current fiber conduit contactor depicted in FIG. 2 may be used for any of the extraction processes described herein or for any other process that may be performed in a fiber conduit contactor/reactor.

Turning back to FIG. 1, during operation of an apparatus such as that depicted in FIG. 1, an extractant liquid, such as an IL, is introduced through tube 14 and onto fibers 12. Another liquid, such as a leachate containing dissolved metal ions, is introduced into conduit 10 through inlet pipe 20 and through void spaces between fibers 12. Fibers 12 will be wetted by the extractant preferentially to the other liquid. The extractant will form a film on fibers 12, wherein the film will be dragged downstream through conduit 10 by the passage of the other liquid therethrough. As a consequence of the relative movement of the other liquid with respect to the extractant film on fibers 12, a new interfacial boundary between the other liquid phase and the extractant is continuously being formed, and as a result, fresh liquid is brought in contact with the extractant, thus causing and accelerating the extraction. One skilled in the relevant art would understand the applicability of various extractant compositions and reaction conditions to achieve the desired result. For example, a phase transfer catalyst or co-solvent can be optionally employed to facilitate mass transfer across the interface between the phases. The phase transfer catalyst and/or co-solvent may be introduced to the conduit reactor in the constrained phase, the continuous phase, or both phases. Useful phase transfer catalysts for reactions include, but are not limited to, quaternary ammonium compounds, quaternary phosphonium compounds, sulfonium compounds, crown ethers, polyglycols, and combinations thereof.

Regardless of the type of liquids used for the constrained and continuous phases, both phases will be discharged into separator 24. In some cases, the volume of the liquid which is not the extractant will be greater in the separator because the extractant may move at a slower velocity than the other liquid phase. In some embodiments, the extractant will collect in the lower portion as it may be heavier (denser) than the other liquid. In other cases, the extractant may be less dense than the other liquid. In either case, because the constrained phase follows the fibers and the liquid phases come out of the conduit reactor separated, the process described herein may be utilized even when the phases are very close in density. Although the embodiment shown in FIG. 1 describes an arrangement wherein the downstream end of fibers 12 extends into separator 24 below interface 30 so that the heavier liquid can be collected directly in the bottom of separator 24 without it being dispersed into the other liquid, the arrangement of fibers 12 is not so limited. In particular, in some embodiments, the downstream end of fibers 12 within separator 24 may be alternatively disposed above or at the interface between the liquid phases within separator 24, depending on the relative density of the constrained phase and the continuous phase. Although the aforementioned example description of FIG. 1 mentions the use of an IL solution as the constrained phase and leachate as the free phase, use of these types of liquids is only an example. Any suitable materials comprising substantially immiscible phases may be employed to effect an extraction or reaction.

Figure 3:
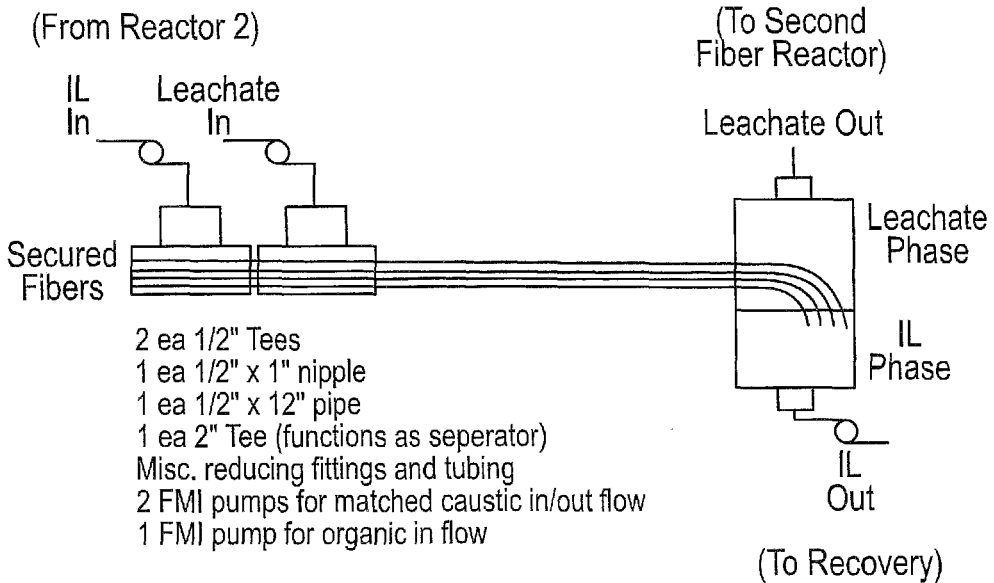
FIG. 3 depicts an example of a fiber conduit contactor system useful for the processes described herein.
Figure 3:
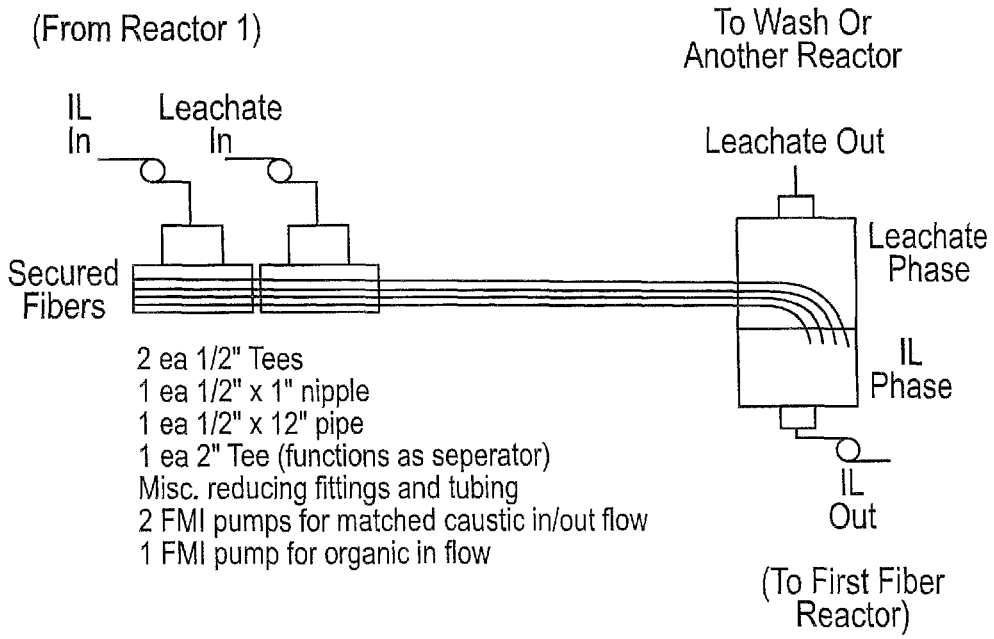

FIG. 3 shows a conduit reactor system useful for the processes described herein. In operation, the secured fibers in Reactors 1 and 2 are wetted by the constrained phase (denoted in FIG. 3 as "IL in") before the mobile phase (denoted in FIG. 3 as "Leachate in") is started. FIG. 3 shows how multiple fiber reactors can be used to increase efficiency of utilization of reactants and to increase extraction of species by essentially feeding the liquids counter-currently through the reactor sequence. The continuous phase output of Reactor 1 (denoted in FIG. 3 as "Leachate Out") is introduced to Reactor 2 (denoted in FIG. 3 as "Leachate In") and further processed thereby. The constrained phase output of Reactor 2 is introduced to Reactor 1 ("IL In") while the constrained phase output of Reactor 1 is processed to remove the concentrated metals (or alternatively introduced to another reactor upstream of Reactor 1 (not shown). In FIG. 3, the constrained and mobile phases are depicted as flowing co-currently through each individual reactor, but the constrained and continuous phases may flow counter-currently through the reactor sequence. In some cases, a fresh IL or a different IL can be used with each reactor if desired. Although the description of FIG. 3 discusses the use of an IL solution as the constrained phase and leachate as the free phase, use of these types of liquid is only an example. Any suitable materials comprising substantially immiscible phases may be employed to effect an extraction or reaction.

Figure 4:
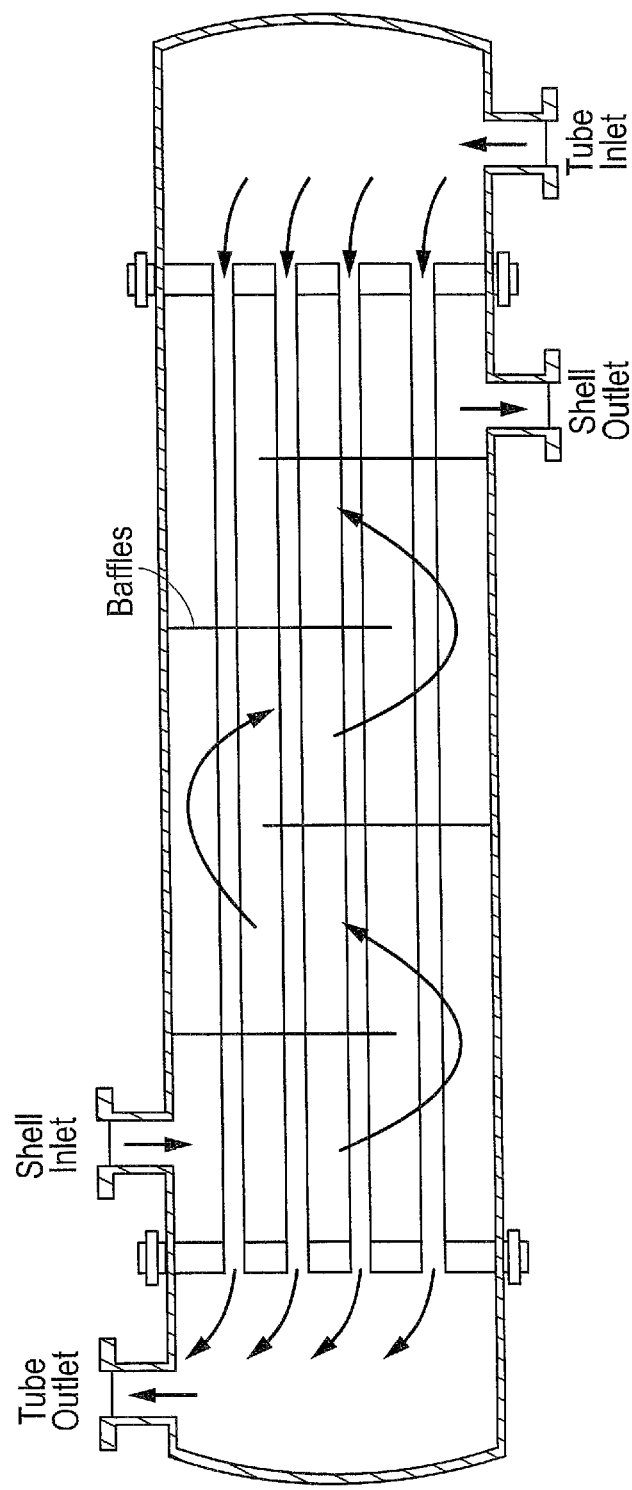
FIG. 4 depicts a shell and tube heat exchanger for incorporation into a fiber conduit contactor.

FIG. 4 shows a conventional shell and tube heat exchanger. Combining this design with a fiber conduit reactor yields a fiber conduit reactor design (not shown) adapted to handle reactions/extractions that need to be cooled or heated. One can see that modification of the inlet of the heat exchanger tubes ("Tube Inlet") to duplicate the inlets shown in FIG. 1 would make each tube in the exchanger act like a thermally controlled fiber reactor (not shown). The exit end of the heat exchanger ("Tube Outlet") can be modified to operate as a separator (not shown) to collect the extract phase, such an as IL, on the bottom near the end of the fibers (not shown) and allow the other liquid phase, such as a leachate, to exit from the top of the separator section. Introduction of a heat exchange medium to the exchanger (via "Shell Inlet") and outflow thereof (via "Shell Outlet") allows for the addition or removal of thermal energy from the exchanger tubes. While FIG. 4 depicts a counter-current flow heat exchanger, a co-current arrangement could also be used in conjunction with the process described herein. In addition, although baffles are shown on the shell side of the exchanger in FIG. 4, the process described herein is not so limited and a heat exchanger without baffles may be employed.

Example 1

This example illustrates the use of a fiber conduit reactor comprising a 12"×½" stainless steel tube containing approximately 550,000 glass fibers 14 inches in length to primarily recover rhenium from waste superalloy. The liquid volume of the reactor was approximately 18 mL. Superalloy powder was dissolved in oxidizing acid. Two different solvent extraction experiments were performed by contacting a stream of approximately 1 ml/min of acid solution of superalloy on the fibers with 1) approximately 1 mL/min of kerosene containing extractants trioctyl amine and tributyl phosphate and 2) approximately 1 mL/min of kerosene containing tributyl amine and aliquat 336. Both experiments were performed at room temperature (i.e., between 20-30° C.). Pressure in the reactor during both experiments was less than 1 psig, indicating little to no accumulation of crud. The phases emerged from the reactor separated and flowed into the receiver. The lower aqueous phase was analyzed for the concentrations of metal ions. Table 1 shows that 91% of the rhenium was extracted in one step when extractants trioctyl amine and tributyl phosphate were used. In the same run, rhenium was selectively extracted compared to tantalum and nickel, which were only about 16% extracted.

Example 2

This example illustrates the use of a fiber conduit reactor comprising a 12"×½" stainless steel tube containing approximately 550,000 glass fibers 14 inches in length to extract and separate rare earth elements from a simulant pregnant leach solution. The liquid volume of the reactor was approximately 18 mL. The simulant pregnant leach solution (PLS) was prepared by dissolving Y and Yb in acid solution. A first experiment was performed by contacting a stream of approximately 1 ml/min of acid PLS solution on the fibers with approximately 1 mL/min of kerosene containing a commercial extractant of bis (2-ethyl hexyl) phosphate. A second experiment was performed with the same solutions, but at approximately twice the flow rate. Both experiments were performed at room temperature (i.e., between 20-30° C.). Pressure in the reactor during both experiments was less than 1 psig, indicating little to no accumulation of crud. The phases emerged from the reactor separated and flowed into the receiver. The upper aqueous phase was analyzed for the concentrations of metal ions. Table 2 shows the first experiment run at flow rates of approximately 1 mL/min for the aqueous acidic simulated PLS and the commercial extractant bis (2-ethyl hexyl) phosphate in kerosene gave excellent extraction efficiencies of 97% of Y and 99% of Yb in one stage. The same solutions run at approximately twice the flow rate yield extraction efficiencies of 81% of Y and 97% of Yb in one stage.

Example 3

Addition extraction experiments were conducted utilizing the PLS solution described in Example 2 in the same reactor described in Example 2 with an experimental extractant developed for solvent extraction of REE. The experimental extract was labeled as "Cyanex 572", but the true identity was not provided. As show in the last two lines of Table 2, excellent results for selective extraction of Yb versus Y were achieved. A 28 minute process time through the fiber conduit reactor gave a separation factor Yb:Y of 206 and a shorter process time, specifically 14 minutes of process time through the fiber conduit reactor, yielded a higher separation factor Yb:Y of 2123.

TABLE 1

Extraction of Rhenium, Tantalum and Nickel from Dissolved Superalloy

| | M in, mg/L | | | M out, mg/L | | | % extraction | | | Distribution Coefficients | | | Separation Factors | |
|---|---|---|---|---|---|---|---|---|---|---|---|---|---|---|
| | Re | Ta | Ni | Re | Ta | Ni | Re | Ta | Ni | DRe | DTa | DNi | $S_{Re,Ta}$ | $S_{Re,Ni}$ |
| 1 | 602 | 13 | 17116 | 57 | 11 | 14151 | 91 | 16 | 17 | 9.6 | 0.2 | 0.2 | 49 | 46 |
| 2 | 397 | 962 | | 222 | 626 | | 44 | 35 | | | | | | |

1 20% Trioctyl Amine/30% Tributyl Phosphate in Kerosene

2 Tributyl Amine and Aliquat 336 in Kerosene

TABLE 2

Extraction and Separation of Y and Yb

| Surrogate solution, (mg/L) | | Surrogate solution after extraction (mg/L) | | % extraction | | | | | Extraction |
|---|---|---|---|---|---|---|---|---|---|
| Y | Yb | Y | Yb | Y | Yb | $D_Y$ | $D_{Yb}$ | $S_{Yb,Y}$ | Time (min) |
| 5252 | 2704 | 144.6 | 22.74 | 97.3 | 99.2 | 35.3 | 118 | 3.3 | 28 |
| 5252 | 2704 | 1021 | 70 | 80.6 | 97.4 | 7.5 | 68 | 9.1 | 14 |
| 5252 | 2704 | 5195 | 830 | 1.1 | 69.3 | 0.01 | 2.3 | 206 | 25 |
| 5252 | 2704 | 5251 | 2043 | 0.02 | 24.4 | 0.0002 | 0.3 | 2123 | 15 |

Lines 1 and 2: Simulated PLS and extractant-bis (2-ethyl hexyl) phosphate in kerosene processed at flow rates of approximately 1 mL/min and 2 mL/min, respectively
Lines 3 and 4: >99% Separation of Yb versus Y from simulated PLS utilizing an experimental extractant at flow rates of approximately 1 mL/min and 2 mL/min, respectively

Example 4: ILs and Organic Solvents in a TALSPEAK Process

This example is modeled from a published batch process experiment which utilized the same process solutions for the noted extraction. The noted data is the same as the published batch process experiment on the presumption that similar if not better results will be achieved using a fiber conduit reactor. In this simulation, a fiber conduit reactor comprising a 36"×½" stainless steel tube containing approximately 550,000 glass fibers 42 inches in length is contemplated for use. The liquid volume of this reactor is approximately 35 mL. Simulated extraction experiments involve contacting a stream of 0.5 ml/min of butyl-1-methylpyrrolidinium bis(trifluoromethylsulfonyl)imide (see, component 1) containing 40 mM of HDEHP (see, Component 2) with a stream of 5 ml/min of lanthanide-containing aqueous solution in the fiber conduit reactor. The phases emerge from the reactor separated. The upper aqueous phase is analyzed for the concentrations of lanthanide ions. The procedure is repeated with diisopropylbenze (DIPB) as the solvent. Table 3 shows simulated distribution coefficients (Dm) using the ½"×36" fiber reactor for lanthanide extraction from aqueous solutions. A distribution coefficient greater than 1 represents an overall preference for the IL phase. In other words, the larger the distribution coefficient, the greater amount of extraction for the noted element.

Component 1

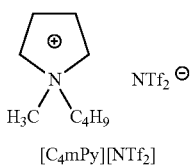

[C4mPy][NTf2]

Component 2

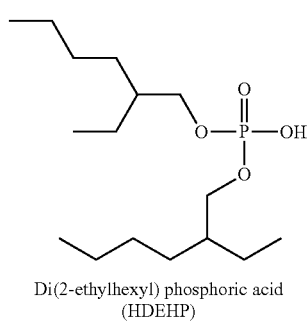

Di(2-ethylhexyl) phosphoric acid (HDEHP)

TABLE 3

Ionic Liquids and Organic Solvents in a TALSPEAK Fiber Process

| | Distribution Coefficient Solvent:Leachate, Dm | | | | | |
|---|---|---|---|---|---|---|
| | La | Nd | Eu | Er | Yb | Lu |
| Ionic Liquid Solvent | 700 | 375 | 75 | 775 | 1175 | 1510 |
| DIPB Solvent | 0 | 0 | 0 | 5 | 60 | 75 |

Example 5: Extraction of Butanol from Fermentation Broth

Biobutanol has received major attention as an alternative fuel and additive to fossil fuels. Biobutanol produced via fermentation is hampered by low butanol concentrations (<1.5%) in the fermentation broth. An efficient separation process is required if biobutanol production is to be economically viable. In this example, liquid-liquid extraction of butanol from water, employing a designed task-specific ionic liquid (TSIL), tetraoctylammoniumnapthenate (TOAMNaph) is simulated and is compared to a simulated process utilizing oleyl alcohol (OA). These experiments are modeled from published batch process experiments which utilized the same process solutions for the noted extraction. The noted data is the same as the published batch process experiments on the presumption that similar if not better results will be achieved using a fiber conduit reactor. For this simulation, parameters for extraction of 1% butanol in water with the two solvents are given in Table 4. Simulating use of the same fiber conduit reactor as Example 1, a solution of 1% butanol in water is pumped through the reactor at 5 mL/min along with 0.4 mL/min of TOAMNaph at 25° C.

The simulated results are given in Table 5. Likewise, a solution of 1% butanol in water is pumped through the reactor at 5 mL/min along with 3.4 mL/min of OA at 25° C. The simulated results are given in Table 5. Note that both OA and TOAMNaph are effective extractants, but the task specific ionic liquid is much more efficient.

TABLE 4

Extraction Parameters for Solvent Extraction of 1% Butanol

|  | OA | [TOAMNaph] |
|---|---|---|
| Selectivity | 194 | 274 |
| Distribution Coefficient | 3.4 | 21 |

TABLE 5

Extraction Results for Solvent Extraction of 1% Butanol

|  | Wt. % Butanol in Water | Wt. % Feed Butanol in Solvent |
|---|---|---|
| Feed | 100 | 0 |
| OA | 29 | 71 |
| TOAMNaph | 5 | 95 |

Example 6: Ionic Liquids and Organic Solvents in Effluent Extraction Fiber Process Distillery effluents are often contaminated streams with chemical oxygen demand (COD) values of up to 48,000 mg/l and low pH values of between 3 and 4. Effluent from a wine distillery consists primarily of organic acids with a high soluble biodegradable COD fraction of up to 98%. Table 6 denotes a typical composition of a wine distillery waste stream with respect to organic acids. This effluent stream must be treated to reduce the COD concentration to acceptable levels for discharge to a municipal sewer.

TABLE 6

Typical organic acid composition of wine distillery effluent

| Tartaric acid | 27% |
|---|---|
| Malic acid | 8% |
| Lactic acid | 29% |
| Succinic acid | 26% |
| Acetic acid | 10% |

The following experiment is modeled from a published batch process experiment which utilized the same process solutions for the noted extraction. The noted data is the same as the published batch process experiment on the presumption that similar if not better results will be achieved using a fiber conduit reactor. Simulating the use of the same fiber conduit reactor as described in Example 1, lactic acid solutions in water and three different trials of n-dodecane containing varying concentrations of ionic liquid extractant Cyphos IL-104 are pumped into the reactor at 5 mL/min at 25° C. The experiment was simulated with trialkylamine as the extractant in n-dodecane. The distribution coefficient (D) for each run is determined. The results are given in Table 7 and shows Cyphos IL-104 is an efficient extractant for this application.

TABLE 7

Ionic Liquids and Organic Solvents in Lactic Acid Extraction Fiber Process

|  | Cyphos IL-104 | | | Trialkylamine |
|---|---|---|---|---|
|  | A | B | C |  |
| Lactic acid in water, kmol/m3 | 1.1 | 1.1 | 1.1 | 1.1 |
| IL in dodecane, kmol/m3 | 0.72 | 0.3 | 0.018 |  |
| Amine in dodecane, kmol/m3 |  |  |  | 0.42 |
| D | 1.8 | 5 | 10.7 | 1 |

IL = Cyphos IL-104, trihexyl-tetradecyl)phosphonium bis 2,4,4-trimethylpentylphosphinate Example 7: Extraction of Dye from Aqueous Stream Azo dyes are commonly used in the leather and textile industries. However, they are not totally consumed in the process and they are frequently not recovered from process water. The leather industry typically discharges 10-15% of the dye in the plant effluent. This creates both environmental and economic issues. There is a need to remove residual dye from the large volume of aqueous effluent. In leather processing, dye-containing effluents can be treated by absorption using charcoals, activated carbons, clays, soils, diatomaceous earth, etc. The disadvantage of adsorption processes is that the adsorbent needs to be regenerated, which adds to the cost of the process, and is sometimes very time-consuming. Chemical treatments for decolorization of wastewater include reduction, oxidation, complexation, ion exchange, and neutralization. Oxidation is the most commonly used chemical decolorization process. Enzymatic reduction/oxidation reactions can decolorize, but the products of azo dye degradation are mostly aryl amines which are more carcinogenic and toxic than the original effluents. The drawback with all of these methods is the duration of the treatment, which normally ranges from 1 to 6 days. Thus, these methods do not provide an acceptable long term solution.

In this example, azo dyes were extracted from water into a neutral ionic liquid demonstrating feasibility to minimize pollution of waste-waters and decrease dye costs. This experiment is modeled from a published batch process experiment which utilized the same process solutions for the noted extraction. The noted data is the same as the published batch process experiment on the presumption that similar if not better results will be achieved using a fiber conduit reactor. Simulating the use of the fiber conduit reactor described in Example 1, an aqueous stream containing red dye is pumped through the reactor at 5 mL/min with an ionic liquid stream at 2.5 mL/min. This is repeated two more times to give 96% removal of the dye as shown in Table 8.

TABLE 8

Extraction of red dyes from an effluent sample into an ionic liquid

| Dye | Abs (nm) | Number Extraction Stages | Residual conc. ($\times 10^{-4}$ g/L) |
|---|---|---|---|
| Red | 523 | 0 | 1.43 |
|  |  | 1 | 0.85 |
|  |  | 3 | 0.05 |

Example 8: Enantioselective Extraction of Optically Active Drug Isomers

There is a growing demand for optically pure compounds in the chemical industries, because the left- and right-handed enantiomers of chiral, bioactive compounds often exhibit different physiological effects on pharmacological activity, the metabolism process, and toxicity when ingested by living organisms. For example, ibuprofen (2-(4-isobutylphenyl)propionic acid (IBU) is used as a nonsteroidal anti-inflammatory drug, which is still sold as a racemic mixture. S-IBU, however, is 28 times more physiologically active than the R-IBU which can cause gastrointestinal toxicity, water retention, and other side effects. Enantioselective chemical production can be achieved by enantioselective methods to separate racemic mixtures. The most common technique for obtaining enantiopure compounds is the separation of enantiomers. Various separation methods including crystallization and chromatography have been developed. Existing methods, however, are not always applicable for most racemic mixtures. Chiral solvent extraction is a potentially attractive technique which is cheaper and easier to scale up to commercial scale and has a large application range. An economically feasible reactive extraction system requires not only high enantioselectivity but also sufficiently fast kinetics. A properly chosen extractant can provide enantioselectivity and a fiber conduit reactor can provide the surface area for fast processing using one or more stages.

The following experiment is modeled from a published batch process experiment which utilized the same process solutions for the noted extraction. The noted data is the same as the published batch process experiment on the presumption that similar if not better results will be achieved using a fiber conduit reactor. Simulating the use of the same fiber conduit reactor as described in Example 1, a solution of 0.1 mol/L of hydroxypropyl-β-cyclodextrin (HP-β-CD) dissolved in an aqueous $NH_2PO_4/H_3PO_4$ buffer solution (pH 2.5) and 1 mmol/L racemic IBU dissolved in cyclohexane are both pumped through the reactor at 5 mL/min at 10° C. The distribution coefficients of IBU enantiomers are determined and are given in Table 9. As shown, cyclohexane/(HP-β-CD) is an enantioselective extractant for racemic IBU.

TABLE 9

Enantioselective Separation of Racemic IBU

| Distribution Coefficient, $P_R$ | Distribution Coefficient, $P_S$ | Enantioselectivity, α |
|---|---|---|
| 3.09 | 3.79 | 1.23 |

Example 9: Extraction of Sulfur Compounds from Diesel

Hydrodesulfurization (HDS) is used for the removal of sulfur compounds in the petroleum refining industry. HDS eliminates aliphatic and non-aliphatic sulfur compounds effectively. But benzothiophene and dibenzothiophene (DBT), type compounds are difficult to remove by HDS. An advantage of some extraction processes is that they can be carried out at normal temperature and pressure. Protic ionic liquids (PILs) have excellent physical and chemical properties as those of traditional ILs but also have unique advantages, such as high extraction efficiency, low cost, low viscosity, easy recycling, and environmental friendly. In this example, the removal of DBT from oil by amine-based PIL dimethylaminopropionitrile propionate [DMAPN][CO2Et] is illustrated. This experiment is modeled from a published batch process experiment which utilized the same process solutions for the noted extraction. The noted data is the same as the published batch process experiment on the presumption that similar if not better results will be achieved using a fiber conduit reactor. Simulating the use of the same reactor as described in Example 1, a 1% DBT solution in n-octane and PIL extractant [DMAPN][CO2Et] are both pumped through the reactor at 5 mL/min at 25° C. The concentration of DBT in the oil was determined for the feed as well as four successions of treating the oil. The results are given in Table 10. As shown, [DMAPN][CO2Et] is an efficient extractant for this application.

TABLE 10

Desulfurization of Oil by PIL [DMAPN][CO2Et]

| Number of Extraction Stages | Residual S Concentration (ppm) |
|---|---|
| Feed | 1600 |
| 1 | 650 |
| 4 | 50 |

Example 10: Extraction of Diacetin, Monoacetin, and/or Glycerol from Biodiesel-Triacetin Mixtures The following experiment is modeled from a published batch process experiment which utilized the same process solutions for the noted extraction with centrifugation between each stage. The noted data is the same as the published batch process experiment on the presumption that similar if not better results will be achieved using a fiber conduit contactor. Simulating the use of the same fiber conduit contactor as described in Example 1, a mixture of biodiesel, triacetin, diacetin, monoacetin and glycerol was introduced into the fiber conduit contactor as the constrained phase at a rate of 5 mL/min. In addition, 0.25 mL/min of deionized water was introduced into the fiber conduit contactor as the continuous phase, yielding an aqueous phase to organic phase ratio of 0.05. The organic mixture was processed through the fiber conduit contactor two more times at the same 0.05 aqueous phase to organic phase ratio. The final organic phase (raffinate) and the mixture of the three aqueous fractions (water extracts) were collected and analyzed as shown in Table 11.

TABLE 11

Extraction of crude biodiesel with water (three stages) at 27.5° C. A:O mass ratio of 0.05 at each stage.

| | Feed | Glycerin Raffinate | Water Extracts |
|---|---|---|---|
| Biodiesel | 80.1 | 94.6 | 0.1 |
| Triacetin | 12.6 | 5.1 | 30.5 |
| Diacetin | 5.9 | 0.1 | 22.7 |
| Monoacetin | 0.9 | 0.0 | 3.9 |
| Glycerol | 0.5 | 0.0 | 2.1 |
| Water | 0.0 | 0.2 | 40.7 |

Example 11: Absorption of $CO_2$ into an Ionic Liquid

The following experiments are modeled from published conceptual experiments which utilized the same process solutions for the noted absorptions. The noted data is the same as the published conceptual experiments on the presumption that similar if not better results will be achieved using a fiber conduit contactor. Ionic liquid 1-n-butyl-3-methylimidazolium acetate [bmim][Ac] was pumped at 1 mL/min over the fibers as a constrained phase in a ½' by 12" fiber conduit contactor. $CO_2$ flowed through the free volume of the reactor at 100 kPa and 30° C. $CO_2$ absorption by the ionic liquid resulted in a weight increase (wt %) of 13.3%. Similar experiments with MEA and MEA:$H_2O$ (50:50 vol) resulted in weight increases of 0.9% and 12%, respectively.

What is claimed:

1. A method of chemical extraction, comprising:
   introducing a first stream comprising an extractant proximate a plurality of fibers positioned longitudinally within a conduit contactor and extending proximate to one or more collection vessels, wherein the first stream constitutes a phase substantially constrained to exterior surfaces of the fibers;
   introducing a second stream into the conduit contactor proximate to the plurality of fibers, wherein the second stream constitutes a phase flowing in alignment and between the fibers that is in contact with and is substantially immiscible with the first stream, wherein the second stream is a fermentation broth or a waste stream from a fermentation process, and wherein the first stream and the second stream are introduced into the conduit contactor such that the extractant of the first stream interacts with the second stream to extract a fermentation product and/or a fermentation byproduct from the second stream into the first stream;
   receiving the first and second streams in the one or more collection vessels; and
   withdrawing separately the first and second streams from the one or more collection vessels.

2. The method of claim 1, wherein the first stream and the second stream are introduced into the conduit contactor such that the extractant of the first stream interacts with the second stream to extract an alcohol from the second stream into the first stream.

3. The method of claim 2, wherein the alcohol is butanol.

4. The method of claim 2, wherein the second stream is an aqueous stream comprising less than 1.5% butanol.

5. The method of claim 1, wherein the first stream and the second stream are introduced into the conduit contactor such that the extractant of the first stream interacts with the second stream to extract an acid from the second stream into the first stream.

6. The method of claim 5, wherein the acid is lactic acid.

7. The method of claim 5, wherein the acid is tartaric acid, succinic acid, acetic acid or malic acid.

8. The method of claim 1, wherein the extractant is an ionic liquid.

9. The method of claim 8, wherein the extractant is a room temperature ionic liquid.

10. A method of dye extraction, comprising:
    introducing a first stream comprising an extractant proximate a plurality of fibers positioned longitudinally within a conduit contactor and extending proximate to one or more collection vessels, wherein the first stream constitutes a phase substantially constrained to exterior surfaces of the fibers;
    introducing a second stream comprising a dye into the conduit contactor proximate to the plurality of fibers, wherein the second stream constitutes a phase flowing in alignment and between the fibers that is in contact with and is substantially immiscible with the first stream, and wherein the first stream and the second stream are introduced into the conduit contactor such that the extractant of the first stream interacts with the second stream to extract the dye from the second stream into the first stream;
    receiving the first and second streams in the one or more collection vessels; and
    withdrawing separately the first and second streams from the one or more collection vessels.

11. The method of claim 10, wherein the dye is an azo dye.

12. The method of claim 10, wherein the second stream is an aqueous stream.

13. The method of claim 10, wherein the extractant is an ionic liquid.

14. The method of claim 13, wherein the extractant is a room temperature ionic liquid.

15. A method of chemical extraction, comprising:
    introducing a first stream comprising an extractant proximate a plurality of fibers positioned longitudinally within a conduit contactor and extending proximate to one or more collection vessels, wherein the first stream constitutes a phase substantially constrained to exterior surfaces of the fibers;
    introducing a second stream comprising a pharmaceutical compound into the conduit contactor proximate to the plurality of fibers, wherein the second stream constitutes a phase flowing in alignment and between the fibers that is in contact with and is substantially immiscible with the first stream, and wherein the first stream and the second stream are introduced into the conduit contactor such that the extractant of the first stream interacts with the second stream to extract the pharmaceutical compound from the second stream into the first stream;
    receiving the first and second streams in the one or more collection vessels; and
    withdrawing separately the first and second streams from the one or more collection vessels.

16. The method of claim 15, wherein the pharmaceutical compound is ibuprofen.

17. The method of claim 15, wherein the pharmaceutical compound is an antibiotic.

18. The method of claim 15, wherein the second stream is a manufacturing broth used to create the pharmaceutical compound.

19. The method of claim 15, wherein the extractant is an ionic liquid.

20. The method of claim 19, wherein the extractant is a room temperature ionic liquid.

* * * * *